(12) United States Patent
Petrich et al.

(10) Patent No.: US 8,173,439 B2
(45) Date of Patent: May 8, 2012

(54) MEASUREMENT SYSTEM WITH OPTICAL REFERENCING

(75) Inventors: Wolfgang Petrich, Bad Schoenborn (DE); Joachim Hoenes, Zwingenberg (DE); Uwe Kraemer, Ilvessheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/488,153

(22) Filed: Jun. 19, 2009

(65) Prior Publication Data

US 2009/0304247 A1  Dec. 10, 2009

Related U.S. Application Data

(63) Continuation of application No. PCT/EP2007/011233, filed on Dec. 20, 2007.

(30) Foreign Application Priority Data

Dec. 20, 2006 (EP) .................................... 06026395

(51) Int. Cl.
*G06K 9/00* (2006.01)

(52) U.S. Cl. .......................... 436/164; 382/128; 382/100

(58) Field of Classification Search .................. 436/164; 382/128, 100
See application file for complete search history.

(56) References Cited

U.S. PATENT DOCUMENTS

| | | | |
|---|---|---|---|
| 5,132,097 A | 7/1992 | Van Deusen et al. | |
| 5,408,535 A * | 4/1995 | Howard et al. | 382/128 |
| 5,485,527 A * | 1/1996 | Bacus et al. | 382/128 |
| 6,249,593 B1 | 6/2001 | Chu et al. | |
| 6,420,128 B1 * | 7/2002 | Ouyang et al. | 435/14 |
| 6,993,172 B2 | 1/2006 | Connell et al. | |
| 2004/0071331 A1 | 4/2004 | Lawless et al. | |

FOREIGN PATENT DOCUMENTS

| | | |
|---|---|---|
| EP | 0469377 B1 | 2/1992 |
| EP | 1359409 B1 | 4/2003 |
| WO | WO 00/20535 | 4/2000 |
| WO | WO 00/60029 | 10/2000 |
| WO | WO 03/087272 A1 | 10/2003 |
| WO | WO 03/087273 A1 | 10/2003 |
| WO | WO 2005/021688 A1 | 3/2005 |
| WO | WO 2005/026297 A1 | 3/2005 |
| WO | WO 2005/086854 A2 | 9/2005 |
| WO | 2006096210 A2 | 9/2006 |

OTHER PUBLICATIONS

Keith Owen and Trevor Coley, Automotive Fuels Reference Book, Second Edition, 1995, 2 pages, Published by: Society of Automotive Engineers, Inc., Warrendale, PA.
List of Commonly Encountered Petroleum and Petroleum Products, Florida Department of Environmental Protection, May 11, 2006, 6 pages.

* cited by examiner

*Primary Examiner* — Christine T Mui
(74) *Attorney, Agent, or Firm* — Krieg DeVault LLP

(57) ABSTRACT

A system is described for determining the concentration of an analyte in a liquid by absorption measurement comprising a test element with a detection area which contains at least one reaction area with reagents for detecting the analyte which cause a change in the absorption behavior upon reaction with the analyte. The detection area contains at least one reference area in which the absorption behavior is substantially not changed when wetted by a sample having the analyte. Furthermore, the system contains a detection unit for the spatially resolved detection of light intensities which are received from the detection area and an evaluation unit for evaluating signals from the detection unit. Further embodiments of the system comprise reaction areas and reference areas arranged alternately in two dimensions.

24 Claims, 2 Drawing Sheets

MEASUREMENT SYSTEM WITH OPTICAL REFERENCING

CLAIM OF PRIORITY

The present application is a continuation application based on and claiming priority to International Patent Application PCT/EP2007/011233, filed Dec. 20, 2007, which claims priority to European Patent Application 06026395.1, filed Dec. 20, 2006, the disclosures of each of which are hereby incorporated by reference in their entireties.

TECHNICAL FIELD OF THE INVENTION

The present application relates to the determination of the concentration of an analyte in a liquid using an optical measurement technique with referencing.

BACKGROUND

The determination of the concentration of various analytes in physiological samples is of growing importance in our society. Such samples are analyzed in various fields of application e.g. in clinical laboratories or in home monitoring. In this connection the results are of major importance for the treatment of various diseases. This also especially includes the measurement of glucose in diabetes management and the measurement of cholesterol in the case of cardiac and vascular diseases. Medical blood diagnostics typically requires the collection of a blood sample from the individual to be examined.

The analytics carried out after the blood collection process are often carried out in a small, portable measuring device, a so-called handheld device in which test elements wetted with blood are analyzed. These handheld devices are of major importance especially in the diagnosis of diabetes diseases. In these devices the measurement is primarily carried out electrochemically or optically. In the case of optically-based measurements, the sample is illuminated with light and the reflected light is detected in order to determine the analyte concentration. Test elements such as test strips are primarily used for this which are wetted with the sample such as blood or interstitial fluid on a detection area which is part of the test element. The sample subsequently reacts with the reagents which are applied in or on the detection area. This can lead to a change in color or also in the case of an electrochemical reaction to changes in charge which can then be detected.

In the case of an optical evaluation of detection areas on which only small amounts of sample have been applied, it is very important that the wetted area of the detection area is optimally evaluated. This can be achieved by using reference areas, in addition to an adequate illumination and detection. The referencing can be carried out in various ways. Thus, a reference area which is separated from the detection area can be used thus enabling technical effects such as the properties of the light source or of the detector as well as certain properties of the test element to be compensated. In order to be able to carry out a referencing with regard to sample properties, the reference area should have a similar construction to the detection area.

One example of referencing in a reflectometric system for determining light intensities of a colored spot uses the area surrounding the spot for referencing. The disadvantage of this method is that the background signal for referencing is not wetted by the sample and therefore has other optical properties than the area wetted with sample. One exemplary disclosure in this regard is U.S. Patent Application Publication No. 2004/0071331.

In other methods for determining an analyte concentration in a sample, a distinction is made between two subareas having different binding activities to the analyte in the sample. A binding partner carrier is immobilized in the subarea having a higher binding activity which binds the analyte when the sample is applied. No binding partner is immobilized on the carrier in the subarea with less binding activity towards the analyte. The area with less binding activity is used for referencing. A disadvantage of this analytical system is that with this analytical method it is only possible to carry out and reference reactions which require binding of the analyte to a carrier-immobilized binding partner such that diffusion of the analyte is no longer possible. The determination of the analyte is limited to bound molecules. An exemplary disclosure in this regard is EP 0 469 377.

In yet another referencing method relating to a system for detecting an analyte on a test carrier, the analyte is bound to a receptor immobilized on the test carrier. Part of the test carrier which contains no immobilized receptor is used as a reference. In some instances, the determination of the analyte requires a binding to an immobilized component. An exemplary disclosure in this regard is issued U.S. Pat. No. 6,249,593.

Based on the disadvantages of the prior art, it is an object of the present invention to provide an analytical system for determining the concentration of an analyte which requires no irreversible binding of the analyte to the test carrier.

Another object of the present invention is to provide an analytical system which enables a more accurate determination of analytes using very small sample volumes.

SUMMARY

These objects and other objects that will be appreciated by persons of ordinary skill in the art are achieved by the embodiments of the present invention. In one such embodiment, a system is provided for determining the concentration of an analyte in a liquid by absorption measurement comprising a test element with a detection area which contains at least one reaction area with reagents for detecting the analyte which cause a change in the absorption behavior upon reaction with the analyte, wherein the detection area contains at least one reference area. Furthermore, the system contains a detection unit for the spatially resolved detection of light intensities which are received from the detection area and an evaluation unit for evaluating signals of the detection unit. The system is characterized in that the at least one reference area is configured such that the optical absorption behavior does not substantially change upon wetting with a sample having the analyte.

In this connection, embodiments of the detection area can have various shapes. It can for example be angled or round. In one embodiment, the shape of the detection area is quadratic or rectangular. The detection area thereby has a length and a width. The area spanned by the length and width has at least one reaction area as well as at least one reference area.

The at least one reaction area differs from the at least one reference area in that, for the latter, substantially no change of the optical absorption behavior takes place due to the analyte in the reference area. This can be achieved in one embodiment in which the reference area has no reagents which can react with the analyte. Another possibility of keeping the change in the absorption behavior in the at least one reference area as small as possible is to avoid the wetting of the at least one reference area by the sample.

In one embodiment of the present invention, the sample is prevented from coming into contact with the reference area by the geometric arrangement of the reference area in relation to the reaction area. Thus, for example a barrier can be present between the two areas. In addition to separating the reference area by a barrier, the reference area can also be arranged at a displaced level relative to the reaction area so that when sample is applied to the detection area, the reference area is not brought into contact with the sample. When the sample is applied to the detection area which can for example be achieved by using a capillary or absorbent materials, the reference area can be at such a distance from the application position that the sample liquid cannot come into contact with the reference area due to the selected distance between the reference area and application site. In a particular embodiment, liquid sample which for example has been taken up by a needle structure is applied by contacting the detection area with the needle structure in a targeted manner. The targeted (e.g. automated) contacting of the detection area with the needle structure can have the effect that only selected areas of the detection area come into contact with liquid.

In a further embodiment the sample comes into contact with the reaction area as well as with the reference area. The reference area is configured such that its absorption behavior is substantially unchanged when wetted with liquid sample having the analyte. The minimal change of the absorption behavior in the reference areas is due to properties of the sample which is applied as a liquid (such as for example serum, blood or urine) to the detection area. These properties for example include the refractive index which changes on the detection area when a liquid is applied to the detection area because the air which is displaced by the liquid has a different refractive index to the applied liquid. However, solid components or dyes as well as other components of the liquid sample are also among the properties which influence the absorption behavior without being able to deduce the presence of an analyte from these properties. Since the change in the absorption behavior in the reference area is only a small fraction of the absorption behavior change due to the change in the analyte in the reagent area, one can speak of a substantially unchanged absorption behavior. In this connection the change in the absorption behavior in the reference areas is typically no more than about 30% of the original absorption, and no more than about 5% in some embodiments and no more than about 1% in yet other embodiments.

In a particular embodiment of the present invention, several reaction areas and several reference areas are arranged alternately in two dimensions. Alternately in two dimensions generally means that at least one reaction area and at least one reference area are located alternately in the detection area on the area on which the reaction areas and the reference areas are located. This is independent of the plane from which the area is viewed. In this connection the two dimensions span the base area of the detection area and the axes of the two dimensions are arranged at right angles to one another. As a consequence, at least one reaction area and at least one reference area are arranged in the one dimension as well as in the second dimension. In this case the individual areas can have different shapes and sizes.

When sample liquid is applied to the detection area, the analyte reacts with reagents for the detection of the analyte at least in the at least one reaction area. During this reaction of the analyte with the reagents, the optical absorption behavior of the at least one reaction area wetted with sample liquid changes. In some practical applications, the reagents contain at least one enzyme which in one embodiment is immobilized on the detection area. Some of the reaction products of this enzymatic reaction can serve as an intermediate product for a further enzymatic reaction or an end product of the enzymatic reaction can itself change the absorption behavior in the reaction area. In both cases (end product or intermediate product) a dye is formed in the course of the reaction which changes the absorption behavior of the reaction area. The change in the optical absorption behavior takes place due to the reaction of the analyte with at least one reagent in the reaction area. In this process the absorption can increase or decrease at the irradiated wavelength. In one embodiment, the absorption increases because a dye can be formed in a reaction which absorbs light at the irradiated wavelength. The light which is reflected or transmitted from the detection area can be detected with the aid of a detector.

In one embodiment of a system in which the absorption behavior in the reaction area is changed due to the formation of a dye, the reaction changing the absorption behavior from the reaction area does not take place in the reference area(s). This may be for various reasons which are described below as examples:
1. There is no enzyme whatsoever in the reference area(s).
2. The at least one enzyme was deactivated in the reference area(s).
3. The color-generating reaction does not proceed in the reference area(s).
4. An additional coating of the reference area at least partially prevents the wetting of the reference area with sample.
5. The reference area is not wetted with sample.

In this manner the structure of the reference area and its behavior towards the analyte can be designed to be very similar to the reaction area. However, no optical absorption change due to the analyte occurs in the reference area. The first three variants can ensure that the properties of the sample are taken into consideration in the referencing which increases the accuracy of the measurement results. They can be used in systems which have test elements or detection areas that are as small as possible because the measurement signals of miniaturized systems are very small and thus error-prone. Referencing on areas of the detection area that are as identical as possible in which irregularities of the test element as well as of the sample are taken into consideration allows a very small amount of sample to be still evaluated sufficiently accurately.

In order to prevent the dye that is formed from diffusing from the reagent areas into the reference areas, a dye can be selected which is insoluble in water after it has been formed by the reaction of the analyte with the reagents. As a consequence, the dye precipitates in aqueous solution (such as for example blood) and no diffusion of the dye can take place into neighboring areas such as for example the reference areas.

The arrangement and/or shape of the reagent and reference areas can be chosen at random or can be uniform. In one embodiment, the reaction and reference areas have different sizes and the at least one reference area can be smaller than the at least one reaction area. In a further embodiment, several reagent and reference areas are in a regular arrangement. In this case the reaction and reference areas can have the same size and/or the same volume. In order to be able to evaluate small sample volumes, the areas of the reaction and reference areas should be selected to be as small as possible. Since the dimensions of the detection area are typically only a few square millimeters in size, the area of the reaction and reference areas is typically also a few square millimeters. The smallest possible size of a detection area depends, on the one hand, on the choice of production process for the reaction and reference area and, on the other hand, on the accuracy of the detection. If a highly resolving detection system is used, it is possible to optically distinguish between very small areas. In one embodiment, the area of the reaction or of the reference area is <1 mm$^2$. In order to achieve a sufficiently high accuracy in the analysis of the analyte, at least one part of a reaction area and one part of a reference area should be wetted with sample. The smaller the areas, the less sample liquid is required for detecting the analyte in order to obtain an adequate signal of a sufficiently wetted reaction area as well as of an adequately wetted reference area. If the reaction areas and reference areas are arranged alternately in two dimensions as was described for one embodiment, the wetting of a single reaction and reference area with liquid sample is sufficient to determine the concentration of the analyte. In order to be able to measure the smallest possible sample for this, the reaction and reference areas can be selected to be as small as possible so that when the sample is applied at least one reaction area and one reference area are adequately wetted by that sample.

Printing processes and/or knife-coating processes are useful for producing a test element with various reaction and reference areas which are arranged alternately in two dimensions. In this case the detection area can be continuously coated with reagents, after which different parts can be subsequently converted into reference areas by laser irradiation and/or modification of their chemical composition.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1A:
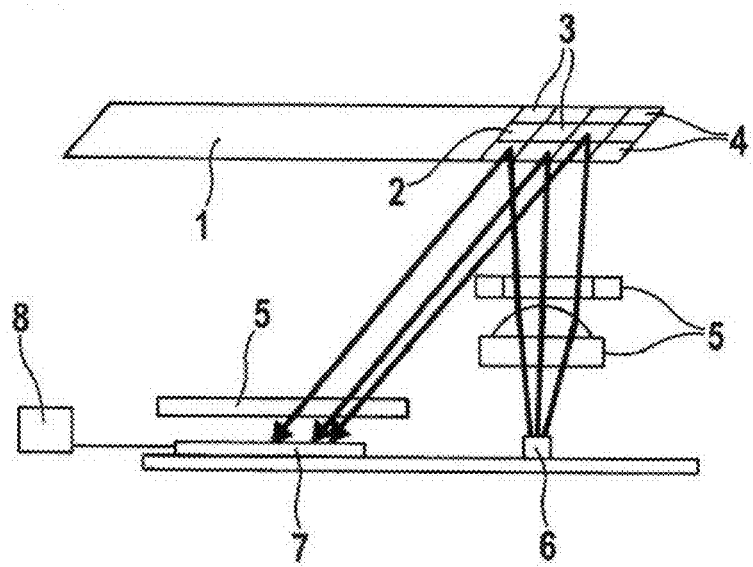
FIG. 1a shows a schematic representation of an embodiment of a system for absorption measurement in a reflective arrangement.
Figure 1B:
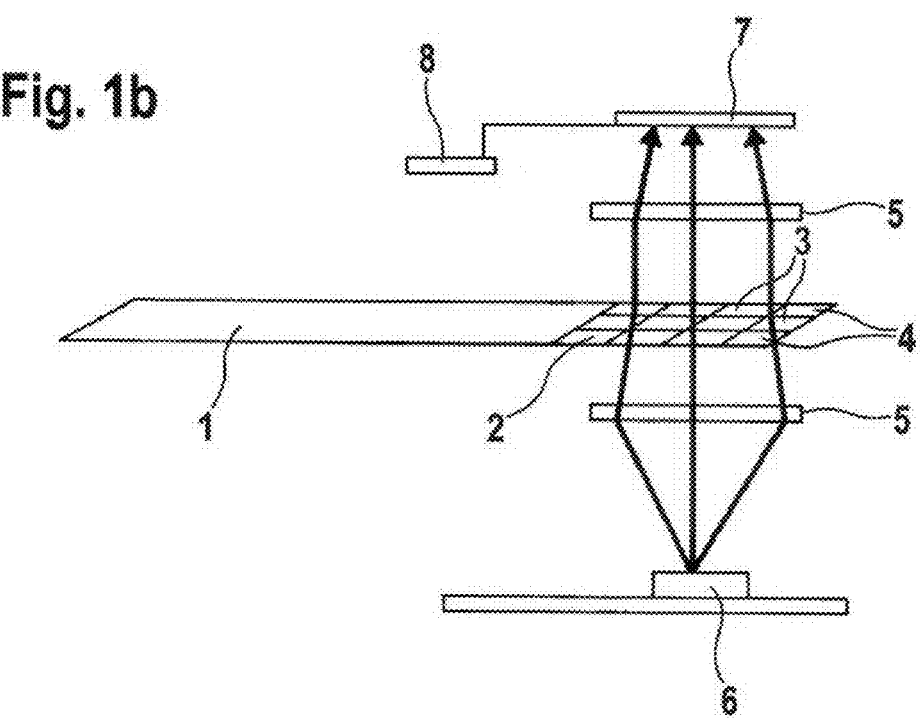
FIG. 1b shows a schematic representation of another embodiment of a system for determining the concentration of an analyte in a transmitted light arrangement.

Embodiments of systems according to the present invention are shown in FIGS. 1a and 1b which show a test element (1) with a detection area (2) which contains several reference areas (4) and reaction areas (3). This system is only shown as an example with several reference areas and reaction areas; systems are also conceivable which only contain one reference area (4) and one reaction area (3).

In FIG. 1a the test element (1) is arranged in the system in such a manner that the detection area (2) is irradiated at least partially by an illumination unit (6) and the light reflected from the detection area (2) is captured by a detector (7). The signals received by the detector (7) can be processed further and evaluated in an evaluation unit (8). In one embodiment, the illumination or detection is spatially resolved, which enables the detection area to be differentiated into the reaction areas (3) and reference areas (4). The signals of the reaction areas (3) and of the reference areas (4) can then be set in relationship to each other and evaluated with an algorithm.

A system is shown in FIG. 1b which again contains a test element (1) as well as an illumination unit (6) and a detector (7) where the detector is arranged on the opposite side of the test element (1) to that of the illumination unit. In this embodiment it must be ensured that at least the detection area of the test element allows the radiation to pass through so that the absorption resulting from the reaction of the analyte with the reagent can be measured with the aid of the detector (7). The illumination and/or detection is also carried out in a spatially resolved manner in this embodiment, which allows the reaction areas (3) and reference areas (4) to be distinguished from one another. In other embodiments, additional imaging units (5) can be used in the system in FIG. 1a as well as in FIG. 1b, provided between the test element and the illumination unit on the one side as well as between the test element and the detection unit on the other side in order to illuminate or detect the test element as effectively as possible. These imaging units (5) can for example be lenses, diaphragms or filters.

Figure 2A:
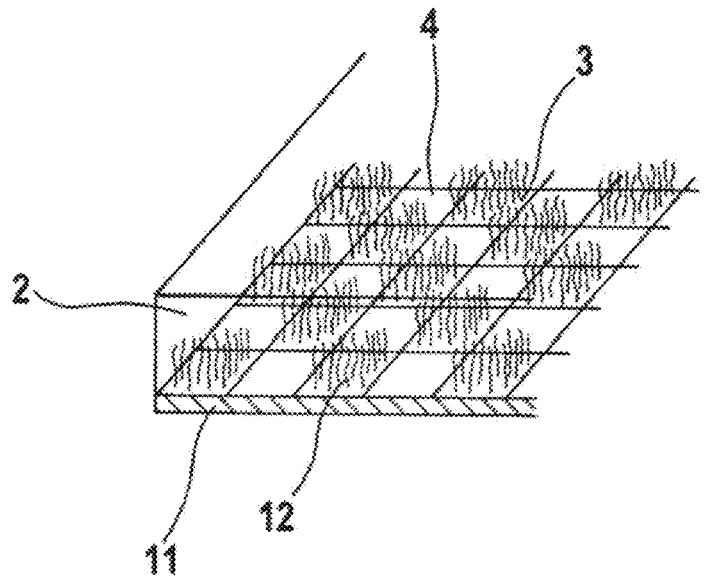
FIG. 2a shows a schematic representation of one embodiment of a configuration of a test element with a detection area which alternately contains several reaction areas and reference areas of generally equal size.
Figure 2B:
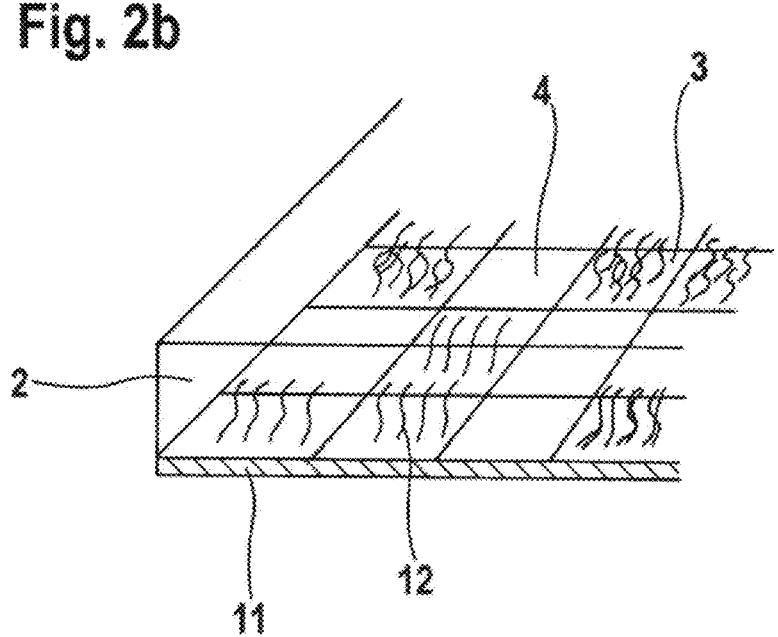
FIG. 2b shows a schematic representation of another embodiment of a configuration of a test element with a detection area which has several alternating reaction areas and reference areas which are of generally different sizes.

The schematic construction of different embodiments of a detection area (2) of a test element (1) are shown in FIGS. 2a and 2b. The test element (1) generally comprises a support foil (11) on which the reagents (12) can be immobilized. The reagent (12) is not immobilized over the entire area of the detection area (2), but rather areas containing immobilized reagent (the so-called reaction areas (3)) alternate with reference areas (4) in which no reagent is immobilized.

A very regular arrangement of reaction areas (3) and reference areas (4) is shown in the embodiment of FIG. 2a, whereas in the embodiment of FIG. 2b a likewise alternating variant of reaction areas (3) and reference areas (4) is shown in which the size of the areas can vary.

Structure of the Reference Area

In one embodiment of the present invention, the reference area is designed to be as similar as possible to the reaction area. In the case of an enzymatic reaction of the analyte with the reagent, the reaction products can usually diffuse away from the site of reaction because the analyte is not bound to the support. For this reason reaction areas and reference areas in the prior art are usually not mounted on the test element in direct vicinity to one another. A direct vicinity of the reaction area and reference area is possible with the present invention, such as in embodiments in which the reactants for the analyte determination are immobilized on a support. One example of this is disclosed in issued U.S. Pat. No. 6,249,593 regarding immunological reactions, where the analyte together with the detection reagent are bound to the immobilized reaction partner. The diffusion processes which occur in analytical systems in which the reaction product is not bound to an immobilized reaction partner can have the result that the reaction product (e.g. dye) diffuses out of the reaction area into the reference area. This impedes a referencing or at least makes it very difficult or even impossible. Various measures can be taken to avoid a spatial separation of the reaction area and reference area and thus to avoid requiring a larger volume of applied sample. On the one hand, the enzyme can be immobilized in the reaction area which results in a spatial restriction of the reaction products. In addition, the dye which forms can be designed to be water-insoluble. In this manner the change in the absorption behavior is limited to the reaction areas. As a result the reaction areas and reference areas can be arranged in direct vicinity and be very small because a diffusion of reagents to be detected is prevented.

Since no reaction which changes the absorption behavior takes place in the reference area, the analyte or intermediate products can diffuse into the reaction areas when the reference areas are wetted because at least the reaction step forming the dye no longer takes place in the reference areas. In order to make this diffusion comparable over the entire detection area, it is possible to choose an arrangement of reference and reaction areas which alternates in two dimensions. In this case the size and shape of the areas is not limiting. However, a uniform distribution of reference and reaction areas is useful in order to ensure a comparable diffusion into all areas and thus a comparability of the areas. This is possible, for example, in a chess-board like arrangement of reference and reaction areas.

As an alternative to inactivating enzymes by a laser or not applying enzyme in the reference areas, the reaction of the analyte with reagent in the reference areas can be prevented by introducing a substance into a part of the reference area which prevents the penetration of the analyte into this area. This may be a membrane which, although being permeable to water molecules, prevents the penetration of larger molecules such as the analyte. Alternatively it is also possible to generally prevent the penetration of liquid. This can for example be achieved by a hydrophobic substance such as for example a hydrophobic plastic or an artificial resin which prevents the penetration of liquid and thus also of analyte. Such plastics and artificial resins are adequately well-known in the prior art.

Enzyme/Coenzyme Composition

The choice of reagents depends on the form of the analyte whose concentration is to be determined. All substances soluble in a liquid can serve as analytes. In one embodiment, this analyte is dissolved in a body fluid, analytes such as typical target molecules in blood like cholesterol, glucose, triglycerides, urea, uric acid or $HbA_{1c}$. Various enzymes such as for example dehydrogenases (e.g. Gluc-DH), oxidoreductases (e.g. GlucDOR) together with coenzymes such as flavin (e.g. FAD/FADH), nicotine (e.g. NAD/NADH) or quinone derivatives (e.g. Q, PQQ) can be used for this. These enzyme/coenzyme systems are sufficiently known in the prior art and are described for example in U.S. Patent Application Publication No. 2005/0214891. In one particular embodiment, glucose is the analyte and can for example be detected by the following enzymatic reactions:

1. By means of GOD-FAD, POD-heam and precipitation of the leuco dye at the site of the immobilized POD.
2. By means of glucose dye oxidoreductase (GlucDOR-PQQ), mediator and immobilized phosphomolybdic acid pyrroloquinoline quinone (PQQ).
3. By means of Gluc-DH-assisted conversion of NAD into NADH with subsequent conversion of a tetrazolium salt using immobilized diaphorase in which formazan precipitates in the last step.

In one embodiment of the present invention, one component in the reaction chain is immobilized. This is typically the component which is at the end of the reaction chain from which the substance changing the absorption behavior is formed. Thus, for example, the glucose-specific enzyme such as GOD, GlucDOR or GlucDH is immobilized in the reaction areas alternately with the reference areas in a chess-board-like pattern on a foil of the detection area.

In order to measure different analytes simultaneously in one sample on a test element, it is possible to introduce different enzymes into different reaction areas.

Production Process

The structuring of the detection area into reference and reaction areas can, in addition to other conventional production processes as described in U.S. Pat. No. 6,592,815 or U.S. Pat. No. 7,008,799, be for example produced with the aid of various printing or coating processes:

screen printing
offset printing
inkjet printing
knife coating.

With the aid of these processes it is possible in one step to structure the surface of the detection area which is located on a support material as is usual for the construction of test elements in such a manner that it has different areas with different functionalities. Thus, the reaction areas can be printed with all necessary reagents whereas some of the reagents are not applied in the reference areas. Alternatively the detection area can be printed similarly to the reaction areas and subsequently the reference areas are deactivated so that the enzymes in the reference areas can no longer react with the analyte. This deactivation can for example take place by irradiation with laser light or by the targeted application of inactivating substances such as for example acids or bases. Alternatively a substance can also be added to the reference areas which irreversibly binds to the enzyme and blocks this enzyme for a reaction with the analyte.

Detection

The detection area can be illuminated by one or more light sources. In this connection the detection area can be homogeneously illuminated or only in subareas. If only one light source is used, a homogeneous illumination of the detection area can be improved by using a milk glass or other scattering units.

An alternative to illuminating the detection area with at least one light source is to utilize the ambient light (sunlight or artificial illumination) to illuminate the detection area. Since the ambient light is multispectral, a filter can be inserted between the test element and detector in order to detect only a certain wavelength range.

Alternatively the system can be provided with different illumination units for the sequential illumination of the test element. This is, however, not absolutely necessary. A simple laser diode combined with a reflector which can be adjusted by a micromechanism can for example be used as the light source. The light beam can scan the test element without gaps with the aid of the reflector. Alternatively a laser array can be used, such as a VCSEL array (vertical cavity surface emitting laser). Each laser in the array can be individually addressed in this case. One helpful aspect of the VCSEL is that the light is irradiated with a low beam divergence. These laser structures have a beam divergence of about 5-8°. In this manner it is not only possible to irradiate a small area but in addition the light quantity on this area is very high.

The illumination unit can consist of a monochromic or multispectral, coherent or incoherent radiation source. The radiation from the illumination unit is used to penetrate into the detection area in order to measure the color reaction of a reagent with the analyte. In certain embodiments, the illumination unit comprises one or more LEDs the light of which ensures either a specially selected spatial intensity distribution or a homogeneous illumination at the sample site. In another embodiment, light having a wavelength of about 660 nm is used. This can be realized by the choice of light source or by incorporating imaging units such as filters which are only light-permeable for a defined wavelength range.

An imaging unit can be mounted between the illumination unit and the detection area. This imaging unit consists of optical elements such as lenses, filters, mirrors, diaphragms, prisms, light conducting or holographic elements. This ensures an illumination of the detection area. A further imaging unit serves to project the irradiated sample body onto the detection unit. This imaging unit also comprises imaging optical elements such as lenses, filters, mirrors, prisms, diaphragms, light-conducting or holographic elements. A microoptical lens array can be optionally used in which each individual element forms images of delimited spatial areas of the test element on individual elements of the detection unit. When using a multispectral light source, it is advisable to mount a filter in front of the detector or in front of the test element.

Detection units for use in the present invention can comprise a planar or linear element which enables the spatially resolved as well as the time resolved measurement of the scattered radiation which is imaged from the detection area. This element can be a two-dimensional CMOS array, a CCD array or a linear diode array in which the spatially resolved imaging of the detection area is carried out by means of a scanning process. In many cases a simple photodiode without spatial resolution may also be sufficient. This can for example be used in combination with a spatially resolved irradiation of the detection area.

Measurement Steps

When a measurement is carried out the following steps are performed by the user or by the system operated by the user:
  Application of the sample to the detection area of a test element,
  spatially resolved measurement of the reflected light intensities from the detection area
  determination of the analyte concentration with the aid of the light intensities measured from at least one reaction area and from at least one reference area.

A test element is used for this which comprises at least one reaction area and at least one reference area in which substantially no change in the absorption behavior occurs due to the analyte and/or the sample when the reference area is wetted. Detection systems can be used for the detection such as those that have already been described.

The system and method for determining the concentration of an analyte in a liquid described in this application generally allow for no further referencing being necessary in the device. Hence, it is not necessary to mount an additional reference field in the system or on the test element that is used to achieve an adequate accuracy of the measurement.

The arrangement of reference areas and reaction areas enables these areas to be simultaneously illuminated and/or detected and/or evaluated. A separate illumination or detection of the different areas is not necessary.

Moreover, the patient does not need to pay attention to how he applies the sample to the test element because the size and shape of the at least one reference area and the at least one reaction area ensures that at least a part of the reference area and a part of the reaction area can be used for the analysis.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features arc critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A system for determining the concentration of an analyte in a liquid by absorption measurement, comprising a test element with a detection area which comprises at least one reaction area with reagents for detecting the analyte which cause a change in the absorption behavior in the reaction area upon reaction with the analyte, the detection area further comprising at least one reference area, the system further comprising a detection unit for the spatially resolved detection of light intensities which are received at least from a part of the detection area, and an evaluation unit for evaluating signals of the detection unit; wherein the one or more reference areas are configured such that the absorption behavior does not substantially change upon wetting with the liquid having the analyte.

2. The system according to claim 1, wherein the detection area comprises a plurality of reaction areas and a plurality of reference areas on the same test element.

3. The system according to claim 2, wherein the reaction areas and the reference areas are arranged alternately in two dimensions.

4. The system according to claim 1, wherein the at least one reference area has a coating or impregnation configured to prevent penetration of the analyte from the liquid into the one or more reference areas.

5. The system according to claim 4, wherein the coating or impregnation is a membrane or a plastic or artificial resin.

6. The system according to claim 1, wherein a water-insoluble dye is formed in the one or more reaction areas when the analyte is present to prevent diffusion of the dye into the one or more reference areas.

7. The system according to claim 1, wherein the reagents contain at least one enzyme which reacts with the analyte.

8. The system according to claim 7, wherein the one or more reference areas contain no active enzyme.

9. The system according to claim 1, wherein the arrangement and/or shapes of the one or more reagent areas and of the one or more reference areas is generally random.

10. The system according to claim 1, wherein the one or more reaction areas and one or more reference areas have generally the same size and generally the same volume.

11. The system according to claim 1, wherein the area of at least one reaction area or of at least one reference area is less than 1 mm².

12. The system according to claim 1, wherein transmitted and/or reflected light is detected by the detection unit.

13. A test element for determining the concentration of an analyte in a body fluid by determining the optical density, comprising a detection area which contains a plurality of reaction areas including reagents and a plurality of reference areas; wherein the reference areas are configured such that the optical density of each is substantially not changed when wetted by the body fluid having the analyte.

14. The test element according to claim 13, wherein the reaction areas and the reference areas are arranged alternately in two dimensions.

15. A method for producing a test element for determining an analyte in a body fluid by measurement of an absorption behavior, comprising the steps of providing a support material, and applying a detection area on at least a portion of the support material, the detection area comprising at least one reaction area and at least one reference area; wherein applying the detection area includes applying one or more reagents for detecting the analyte on the portion of the support material, said reagents for causing a change in the absorption behavior when wetted by the body fluid having the analyte; and wherein the one or more reference areas are configured such that the absorption behavior of each is substantially not changed when wetted by the body fluid having the analyte.

16. The method according to claim 15, wherein the one or more reaction areas and the one or more reference areas are arranged alternately in two dimensions.

17. The method according to claim 16, wherein the arrangement and/or shape of each reagent area and of each reference area is generally random.

18. The method according to claim 15, wherein a printing process and/or a knife-coating process is used for applying the reagents.

19. The method according to claim 15, wherein the one or more reference areas are generated by one of irradiating a part of the reaction area with a laser and changing the chemical composition of a part of the reaction area.

20. The method according to claim 15, wherein the one or more reference areas are generated by at least some of the reagents being deactivated in the reference areas by one of laser irradiation and chemical treatment.

21. The method according to claim 15, wherein the one or more reference areas contain at least one substance less than the one or more reaction areas.

22. The method according to claim 15, wherein the one or more reference areas contain at least one additional substance than the one or more reaction areas, the substance generally preventing a reaction with the analyte.

23. A method for detecting an analyte with a test element according to claim 13 comprising the steps of: applying the sample to the detection area, performing a spatially resolved measurement of the reflected light intensities from the detection area, and determining the analyte concentration with the aid of the light intensities measured from at least one reaction area and from at least one reference area.

24. The method according to claim 23, wherein a sample volume of less than 500 nl is applied to the detection area of the test element.

* * * * *